United States Patent [19]

Borgia et al.

[11] Patent Number: 5,158,552

[45] Date of Patent: Oct. 27, 1992

[54] SAFETY TROCAR INSTRUMENT HAVING A RETRACTABLE TROCAR ACTUATED BY RELIEF OF PRESSURE ON THE TROCAR POINT

[75] Inventors: Julian F. Borgia, Danbury; William J. Allen, Stratford; Jeffrey A. Stein, Milford, all of Conn.

[73] Assignee: American Cyanamid Company, Stamford, Conn.

[21] Appl. No.: 787,183

[22] Filed: Nov. 4, 1991

[51] Int. Cl.$^5$ .............................................. A61M 5/18
[52] U.S. Cl. ..................................... 604/165; 604/274
[58] Field of Search ............... 604/164, 158, 165, 166, 604/167, 168, 169, 170, 274

[56] References Cited

U.S. PATENT DOCUMENTS

| | | | |
|---|---|---|---|
| 4,207,887 | 6/1980 | Hiltebrandt et al. | 128/207.28 |
| 4,535,773 | 8/1985 | Yoon | 604/51 |
| 4,601,710 | 7/1986 | Moll | 604/165 |
| 4,654,030 | 3/1987 | Moll et al. | 604/165 |
| 4,874,375 | 10/1989 | Ellison | 604/164 |
| 4,902,280 | 2/1990 | Lander | 604/165 |
| 4,931,042 | 6/1990 | Holmes et al. | 604/164 |
| 4,943,280 | 7/1990 | Lander | 604/169 |
| 4,986,814 | 1/1991 | Burney et al. | 604/166 |
| 5,009,643 | 4/1991 | Reich et al. | 604/167 |
| 5,013,294 | 5/1991 | Baier | 604/26 |
| 5,030,206 | 7/1991 | Lander | 604/164 |
| 5,066,288 | 11/1991 | Deniega et al. | 604/274 |
| 5,073,169 | 12/1991 | Raiken | 604/180 |
| 5,104,382 | 4/1992 | Brinkerhoff et al. | 604/165 |
| 5,104,383 | 4/1992 | Shichman | 604/167 |
| 5,116,353 | 5/1992 | Green | 606/184 |

FOREIGN PATENT DOCUMENTS

| | | |
|---|---|---|
| 0424002 | 4/1991 | European Pat. Off. |
| 0461568 | 12/1991 | European Pat. Off. |
| A479130 | 4/1992 | European Pat. Off. |

*Primary Examiner*—Paul J. Hirsch

[57] ABSTRACT

A safety trocar instrument, for piercing the wall of an anatomical cavity to provide communication with the inside of the cavity, includes a tubular cannula and an elongate trocar having a sharp piercing point. The trocar is mounted for axial reciprocal movement within the cannula between a withdrawn rest position, in which the point is received within and shielded by the distal end of the cannula, a fully extended position in which the point is exposed beyond the distal end of the cannula, and an intermediate retracted position in which the point also is exposed beyond the distal end of the cannula. A retraction spring biases the trocar to its withdrawn position. A latch latches the trocar, in opposition to the retraction spring, for reciprocal movement between the fully extended and intermediate positions. A trip member couples the trocar to the latch member when the trocar moves from the fully extended position to the intermediate position, and trips the latch member when the trocar returns toward the fully extended position to unlatch the trocar and permit it to be moved to the withdrawn position by the retraction spring.

24 Claims, 6 Drawing Sheets

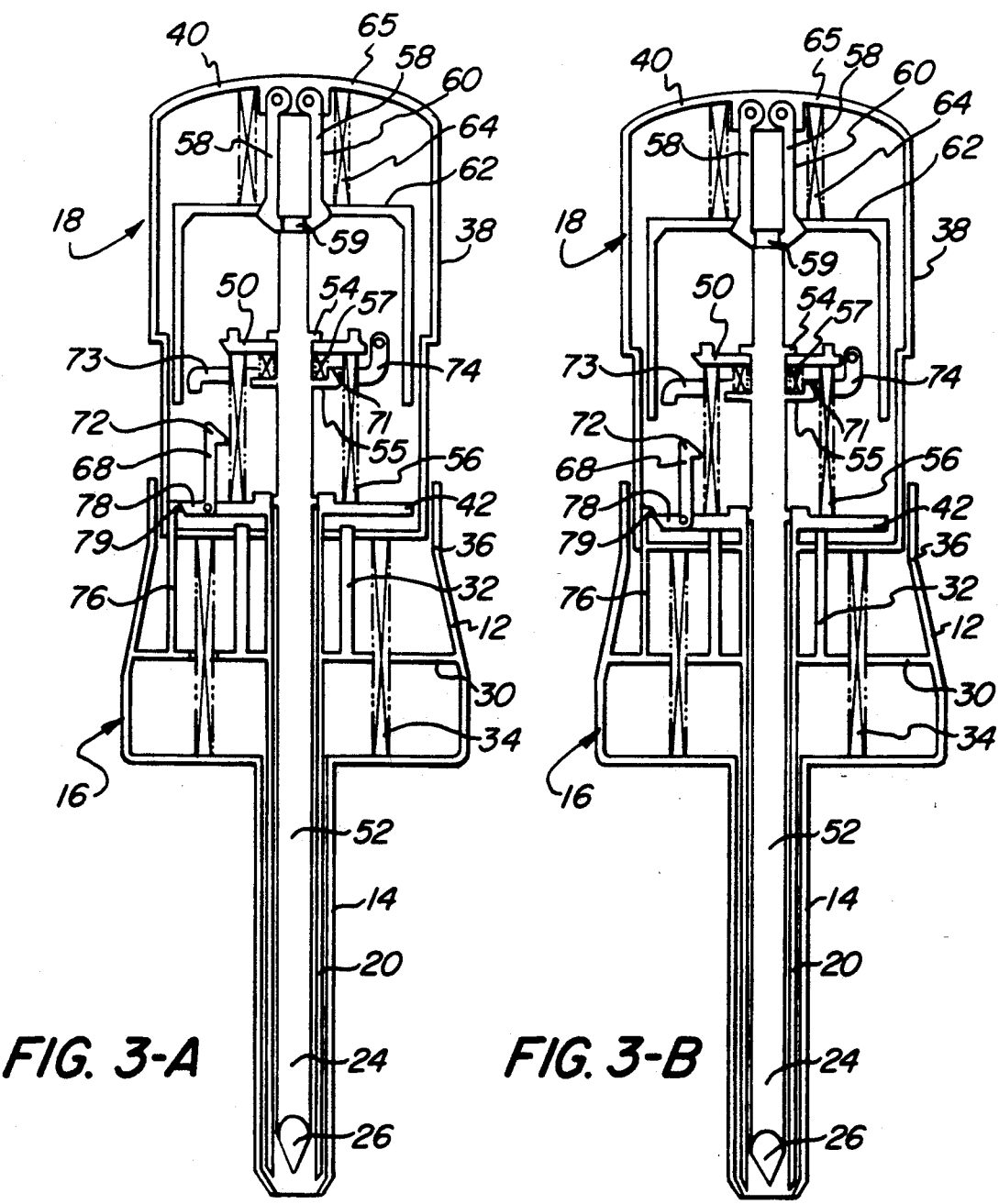
FIG. 3-A   FIG. 3-B

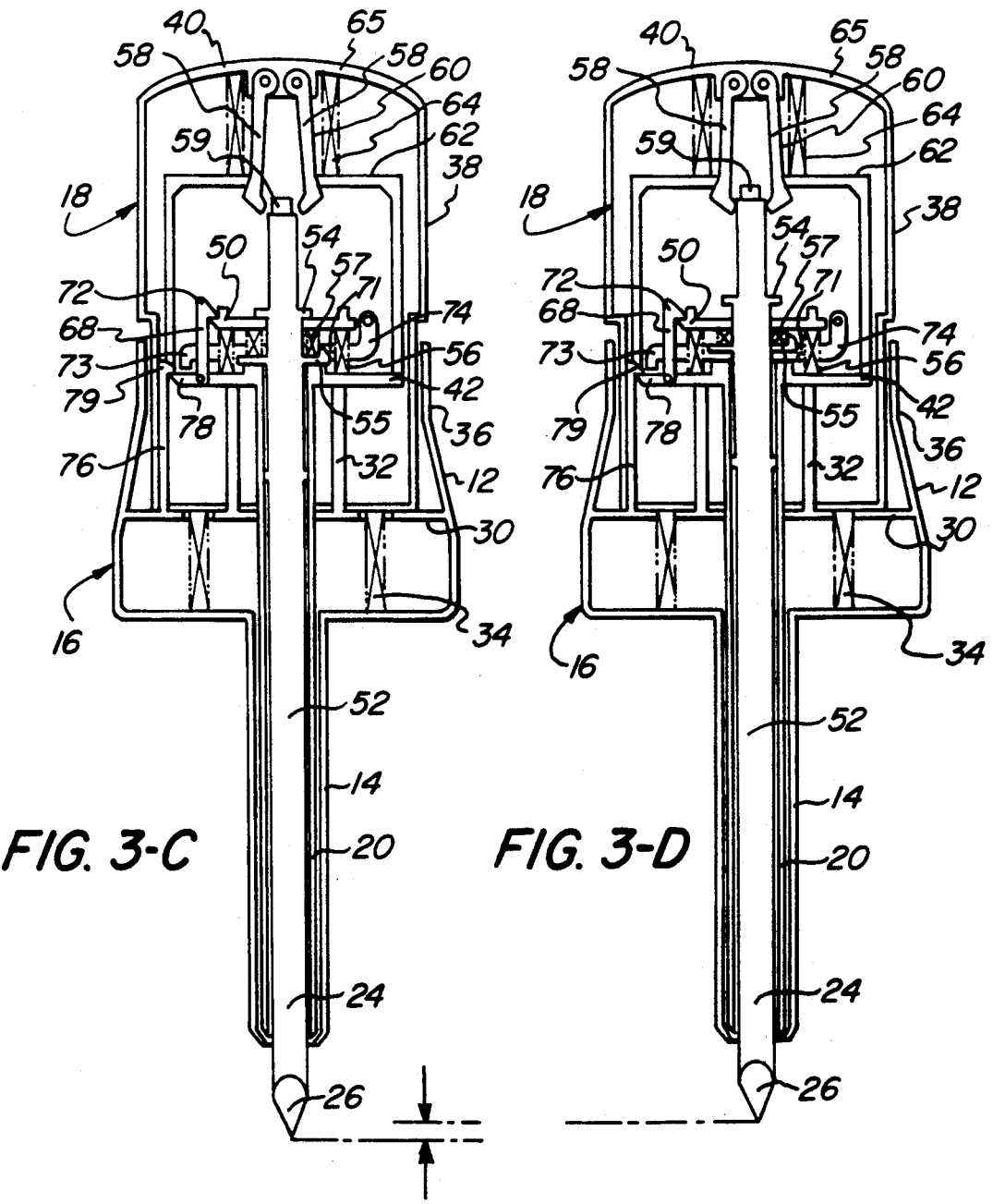

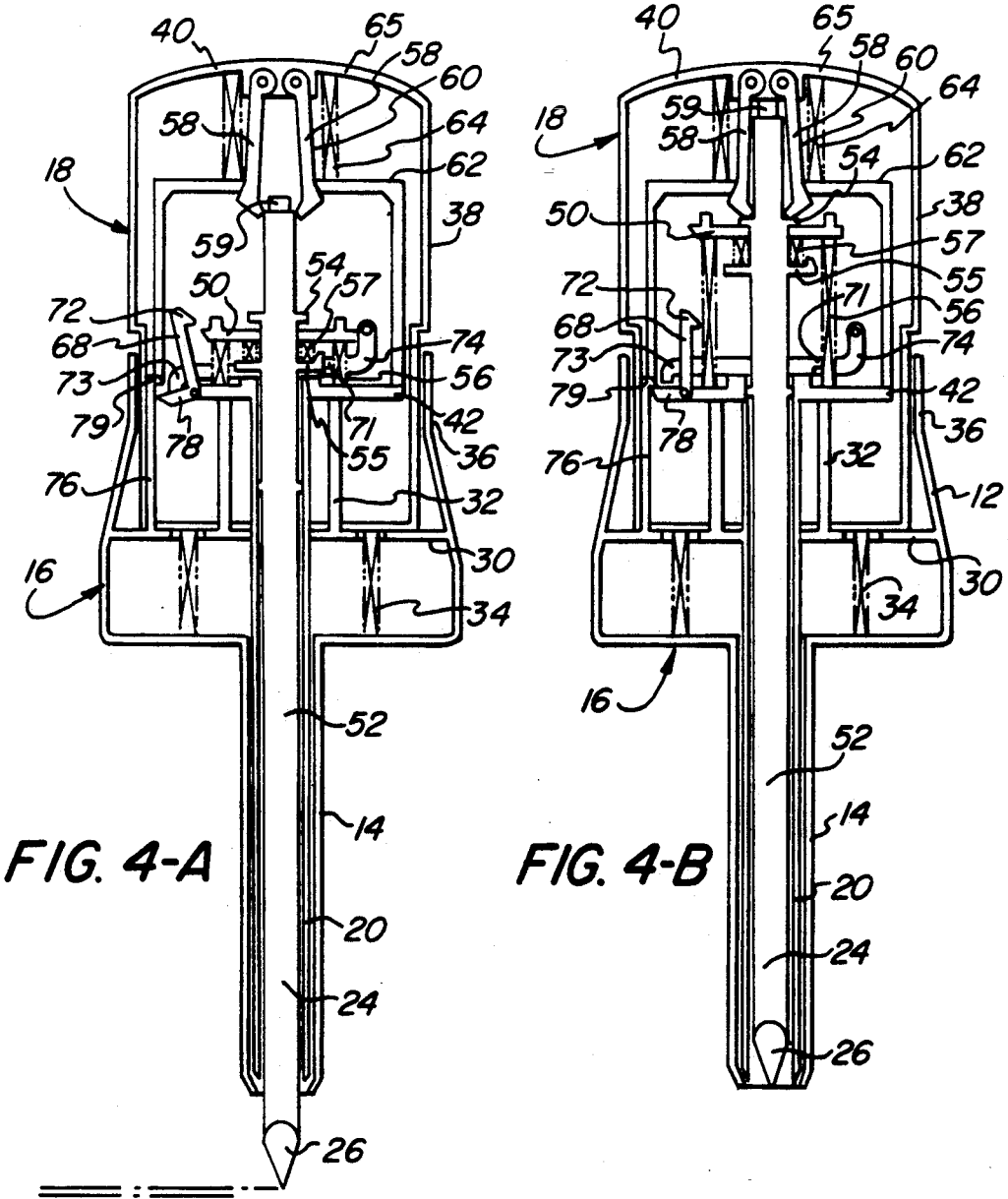

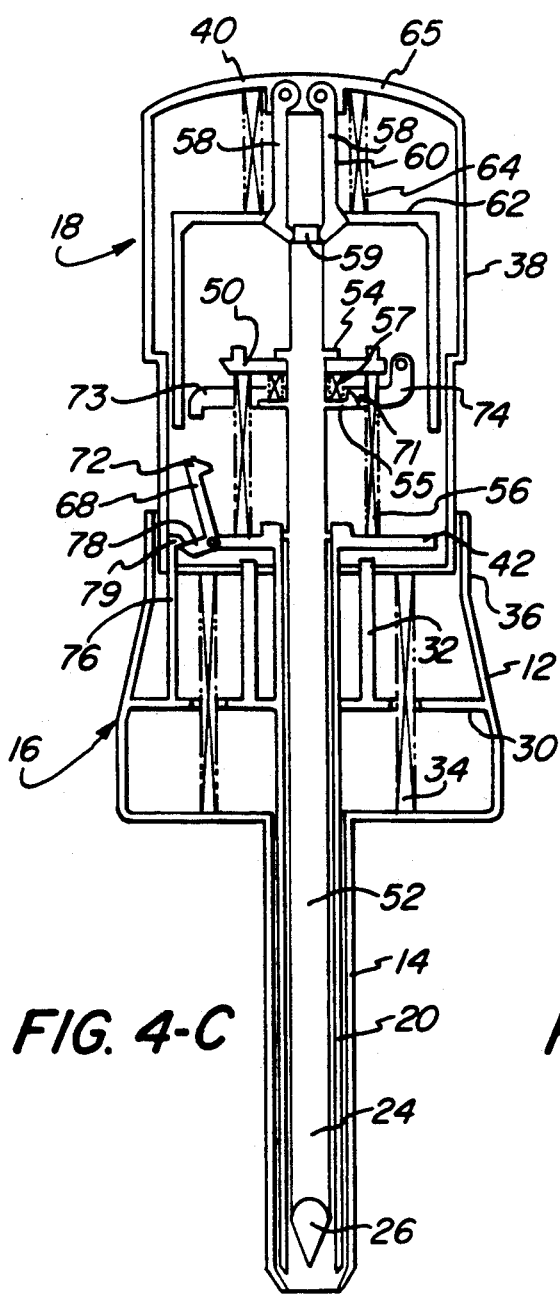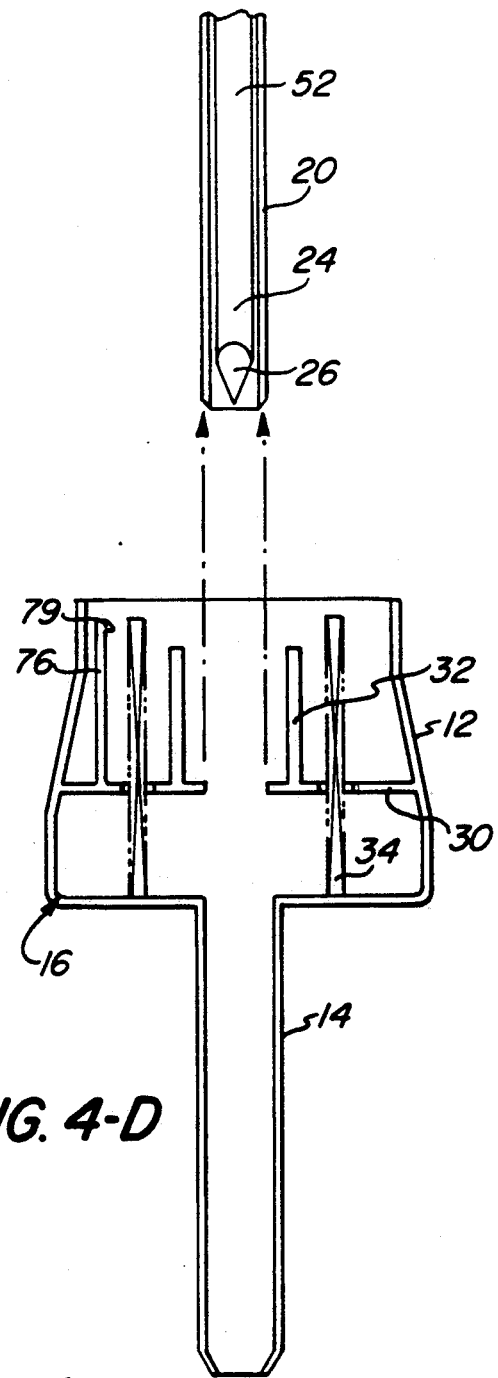
FIG. 4-C   FIG. 4-D

SAFETY TROCAR INSTRUMENT HAVING A RETRACTABLE TROCAR ACTUATED BY RELIEF OF PRESSURE ON THE TROCAR POINT

BACKGROUND OF THE INVENTION

1. Field of the Invention

The present invention relates to a surgical instrument, commonly called a "trocar instrument" or "device," or simply a "trocar," that is used to pierce the wall of an anatomical cavity thereby forming a passageway providing communication with the inside of the cavity. Other medical instruments such as endoscopes, arthoscopes, and operating instruments can thereafter be inserted through the passageway to perform various medical procedures within the anatomical cavity.

Surgical techniques using trocar devices to pierce anatomical cavity walls have recently gained great favor in the expanding field known as "least invasive surgery." Such techniques have been widely employed, for example, in gall bladder surgery and their use for other types of operations is actively being explored and implemented. These methods are desirable because the passageway formed by the trocar is small and neat.

Therefore, the major trauma associated with large surgical incisions, used to perform certain operations in the past, can be avoided.

The present invention provides an improved safety trocar instrument that is well suited to least invasive surgical techniques. By its design the safety trocar instrument of the present invention not only avoids the trauma that results when large incisions are made in an anatomical cavity wall, but also reduces the chance that unintended and unwanted trauma will result particularly after the instrument penetrates the wall.

2. Description of the Prior Art

In its elemental form, a trocar is a device comprising an elongated shaft of, for example, surgical steel having a sharpened blade or point. Typically, least invasive surgery using such a device is performed first by inserting a fine surgical or 'Veress" needle through the cavity wall and thereafter injecting a fluid into the cavity to insufflate it and separate the cavit wall, including muscle and the peritoneum in the case of the abdomen, from other internal organs like the heart, stomach, and major blood vessels. The sharpened point of the trocar is then placed against the cavity wall and urged to pierce it by manually applying pressure to the proximal end of the shaft. An outer sleeve or "cannula" may be slid over the shaft through the wound created by the sharp point. The sleeve permits the shaft to be withdrawn from the cavity wall and maintains the passageway into the cavity. Observation and surgical instruments can then be introduced into the cavity through the sleeve.

Ordinarily, the cavity wall exerts relatively large resistance to penetration by the trocar point.

However, once the wall is pierced that resistance is relieved, often suddenly, so that the sharp trocar point may suddenly be urged deeply into the cavity. Therefore, the risk exists that the sharp trocar point will injure vital organs in the cavity. Accordingly, attempts have been made to reduce that risk.

For example, U.S. Pat. No. 4,654,030 (Moll, et al.) discloses a safety trocar device that includes a trocar subassembly and a trocar tube subassembly that interfit with, but are separable from, one another. The trocar subassembly includes a grip, a trocar or "obturator" having a sharpened piercing tip or point, an axially reciprocally mounted tubular obturator sleeve or shield, and a compressed coil spring for urging the shield forwardly essentially to surround and shield the piercing tip of the obturator. The trocar tube subassembly includes a main body and an elongated trocar tube. The trocar device is used by inserting the obturator and shield of the trocar subassembly into the trocar tube of the trocar tube subassembly. The shield and piercing tip are together urged to extend through the lumen of the trocar tube. Ordinarily, the shield is locked in this extended position. However, when unlocked the shield may withdraw into the trocar tube against the urging of the compressed spring in the trocar subassembly.

In order to pierce an anatomical cavity wall, the shield is first unlocked. Its exposed distal end is placed against the anatomical cavity wall by applying pressure to the assembly. The resistance exerted by the wall causes the shield to retract axially into the trocar tube thereby to expose the piercing tip of the obturator. Thus the tip may puncture the cavity wall. Once the tip and shield have penetrated the wall and have entered the anatomical cavity, the resistance exerted by the wall on the distal end of the shield is relieved permitting it to be urged by the compressed spring back to its extended position surrounding the piercing tip. Accordingly, once the resistance of the cavity wall on the distal end of the shield is released, the chances of injury to internal organ structures are reduced because the sharp portions of the piercing tip are again covered by the shield.

U.S. Pat. No. 4,535,773 (Yoon) also relates to a safety puncturing instrument or trocar for puncturing an anatomical cavity wall and discloses several embodiments of that instrument. A number of the embodiments are conceptually similar to that disclosed in the Moll Patent and include an outer sleeve or obturator tube with an elongated section defining an interior lumen opening at a distal end and extending through to a proximal end. A thin-walled inner sleeve or shield is mounted coaxially within the outer sleeve and is urged by a compression spring to protrude from the lumen at the distal end of the outer sleeve. A trocar or obturator has a sharp blade at its distal end that can be inserted into the inner sleeve so that, when seated, the blade projects beyond the distal end of the outer sleeve but is encircled and shielded by the distal end of the inner sleeve.

These embodiments of the safety puncturing instrument disclosed in the Yoon Patent are used by inserting the trocar into the inner and outer sleeves and placing the distal end of the inner sleeve against the wall of an anatomical cavity. Force is then applied to the proximal end of the trocar so that the outer sleeve and trocar blade are forced toward the cavity wall. The distal end of the inner sleeve is urged to retract within the distal end of the outer sleeve by resistance exerted by the cavity wall, thereby compressing the spring and permitting the trocar blade to be exposed to pierce the wall.

When the outer sleeve enters the wound created by the trocar blade, the inner sleeve is held completely within the outer sleeve by the resistance of the cavity wall to passage of the distal ends of the outer and inner sleeves. As force continues to be applied to the proximal end of the trocar, the sharp point passes through the cavity wall and enters into the cavity. The force also causes the outer sleeve to follow through the wound. As the distal ends of the outer and inner sleeves clear the inner surface of the inside of the cavity wall, the resistance of the wall is relieved thereby releasing the inner sleeve, which is then returned to its extended position by the spring to shield the trocar blade.

Safety trocars like those described above and disclosed in the Moll and Yoon Patents have certain inherent drawbacks. First, because the piercing tip of the trocar blade is generally shielded when the instrument is placed against the anatomical cavity wall, it is necessarily shielded from the surgeon's view. Therefore, he or she cannot be certain that the tip will puncture the wall at the precise location desired. Moreover, after the piercing tip has penetrated the cavity wall, it must protrude a further substantial distance into the anatomical cavity before the inner sleeve or shield is released again to cover the tip. Thus, a substantial period remains during which the tip is exposed and may injure internal organ structures. In the Yoon devices, since the inner sleeve or shield and outer sleeve may remain in the cavity after the trocar is removed, they often project a substantial distance into the cavity. Thus the available space in the cavity within which the surgeon can work is reduced.

The Yoon Patent also discloses another embodiment, shown in its FIGS. 34 and 35, that includes structure for causing the sharp trocar point to retract inwardly into the outer sleeve. More particularly, this structure includes a puncturing implement or trocar having a shaft with a large diameter section at its distal end terminating in a sharp blade and a point that bears one or more electrical pressure sensors or transducer elements. An intermediate section of the trocar has a reduced diameter and is able to slide within a hollow proximal tubular section. A tension spring is coupled between the proximal end of the intermediate shaft section and a plug threaded into the proximal end of the tubular section. A detent mechanism holding a small detent is mounted in the intermediate shaft section. The detent is urged radially outwardly by a compression spring. When the intermediate shaft section is fully extended outwardly from the tubular section, the detent is coaxially aligned with and protrudes radially into a small hole in the wall of that tubular section. Thus, the shaft of the trocar is locked in the fully extended position against the urging of the coil spring, which is then held in tension.

The whole assembly is carried in an outer sleeve. When the trocar is locked in the extended position, its blade extends beyond the distal end of that sleeve.

Electrical leads pass through the interior of the shaft of the trocar and connect the blade sensors to electrical contacts within the detent, and in turn to an electrical socket.

To use the instrument, the trocar is first locked in its outwardly extended position with the detent radially engaged in the detent hole. The trocartubular section assembly is then fitted with a handle and the distal end of the trocar is inserted into the outer sleeve. When that assembly is fully inserted into that sleeve, the detent is coaxially aligned with a radial solenoid socket adjacent the electrical socket. An electrical plug assembly includes an electrical jack that connects the leads from the blade sensors through the socket to an alarm network.

The trocar assembly may then be used by pressing the blade against the anatomical cavity wall such that counterforce exerted by that wall on the blade sensors is converted to a sequential set of ready signals that trigger the alarm network. As the blade passes through the wall into the cavity interior, the counterforce is relieved from the blade sensors sequentially to produce a set of electrical signals through the alarm network. When the penetration is complete, the electrical signals from the sensors cause the alarm network to actuate the solenoid, thereby depressing the detent to permit the tension spring to retract the blade into the sleeve.

An alternative detent structure is illustrated in FIG. 36 of the Yoon Patent.

While in many respects this latter embodiment of the Yoon invention is an improvement over the other safety trocar designs described in the Yoon and Moll Patents, it nevertheless suffers from certain serious disadvantages. First, it depends on electrical pressure sensors or transducer elements connected to an alarm network to sense release of the counterforce exerted by the anatomical cavity wall and thereby to trigger retraction of the trocar point. Therefore, proper operation of the device may be destroyed by an electrical power failure or interruption that, even if brief, can result in serious injury to the patient. Further, the device is not self-contained but must instead be connected to the external alarm network. That alarm network may be cumbersome and the electrical leads connecting the trocar device to the alarm network may well interfere with the surgeon's work.

Therefore, still additional improvement to safety trocar instrument design would be greatly beneficial to the surgical community.

SUMMARY OF THE INVENTION

It is a principal object of the present invention to provide an improved safety trocar instrument that mitigates the problems associated with prior devices of the type disclosed in the Moll and Yoon Patents and having a safety shield that projects forwardly to surround a sharp trocar point after the point and distal end of the shield penetrate an anatomical cavity wall.

It is an additional principal object of the present invention to provide a self-contained, mechanically actuated safety trocar instrument in which a sharp trocar point is retracted into a surrounding sleeve when the sharp point has penetrated an anatomical cavity wall. The invention thereby results in a substantial improvement over known devices such as the latter embodiment described in the Yoon Patent.

These and other objects are achieved by the present invention, which in a preferred embodiment includes a main body that supports an outer sleeve or cannula.

The main body is configured to mate with a trocar subassembly that includes a plunger head and a main housing having a trocar. The trocar has a sharp point.

The safety trocar instrument in accordance with this preferred embodiment is assembled by mating the main body-cannula subassembly with the trocar subassembly such that the trocar is received coaxially within the cannula. The trocar is urged by a retraction spring to a withdrawn rest position with the point surrounded by the distal end of the cannula.

This instrument is armed to pierce an anatomical cavity wall by manually pressing the plunger head of the trocar subassembly into the main body until the sharp trocar point projects beyond the distal end of the cannula with the trocar in a fully extended position. The trocar is initially held in such attitude by an internal latching mechanism residing in the plunger head and main housing of the trocar subassembly. However, the trocar is linked to the latching mechanism through a lost-motion coupling that permits it to be urged backwardly into the housing and plunger head, to an intermediate retracted position, against the force of a pressure spring. The point is nevertheless exposed when the trocar is in the intermediate position.

Once armed, the trocar instrument is used to pierce an anatomical cavity wall by pressing the exposed point of the trocar against the wall at precisely the desired location. During this operation, pressure against the trocar point urges the trocar backwardly through the lost-motion coupling to the intermediate position in a first stage to prepare a trip mechanism for disarming the latching mechanism. When the cavity wall has been completely penetrated, pressure on the trocar point is relieved permitting it again to be returned through the lost-motion coupling by the pressure spring to its fully extended position. The return of the trocar point causes the trip mechanism to fully disarm the latch mechanism thereby releasing the trocar and permitting it to be retracted to its rest position by the retractor spring with its sharp point surrounded by the distal end of the cannula. The trocar subassembly can then be removed leaving the cannula in the anatomical cavity wall to provide communication with the inside of the cavity.

Thus the present invention provides a safety trocar instrument in which the sharp point of the trocar is retracted into a surrounding shield structure. Since retraction occurs immediately upon entry of the trocar point into the anatomical cavity, there is a reduced likelihood of injury to internal organs. Moreover, since retraction occurs promptly at that time, little of the device remains in the cavity after penetration to infringe upon the surgeon's work area. Still further, the trocar point is exposed to the surgeon's view at the start of penetration so that he or she can precisely position it at the desired cavity wall location. Thus the safety trocar instrument of the present invention is a substantial improvement over designs of the type disclosed in the Moll Patents and as the initial embodiments in the Yoon Patent.

The present invention is also entirely self-contained and mechanically actuated. Therefore, it is not affected by electrical power failures or interruptions nor does it depend on cumbersome ancillary electrical equipment. And since no wire connections to such ancillary equipment are required, they are not present to interfere with the surgeon's work.

These and other objects, aspects, features, and advantages of the present invention will become apparent from the following detailed description taken in conjunction with the accompanying drawings.

BRIEF DESCRIPTION OF THE DRAWINGS

FIGS. 3A to 3D are a sequence of vertical cross-sectional views of the safety trocar instrument of the present invention showing it being armed and operated through initial piercing of an anatomical cavity wall; and FIGS. 4A to 4D are a sequence of vertical cross-sectional views of the safety trocar instrument of the present invention showing the trocar retraction operation and the trocar subassembly being removed from the main body-cannula assembly.

DETAILED DESCRIPTION OF THE PREFERRED EMBODIMENT

Figure 1:
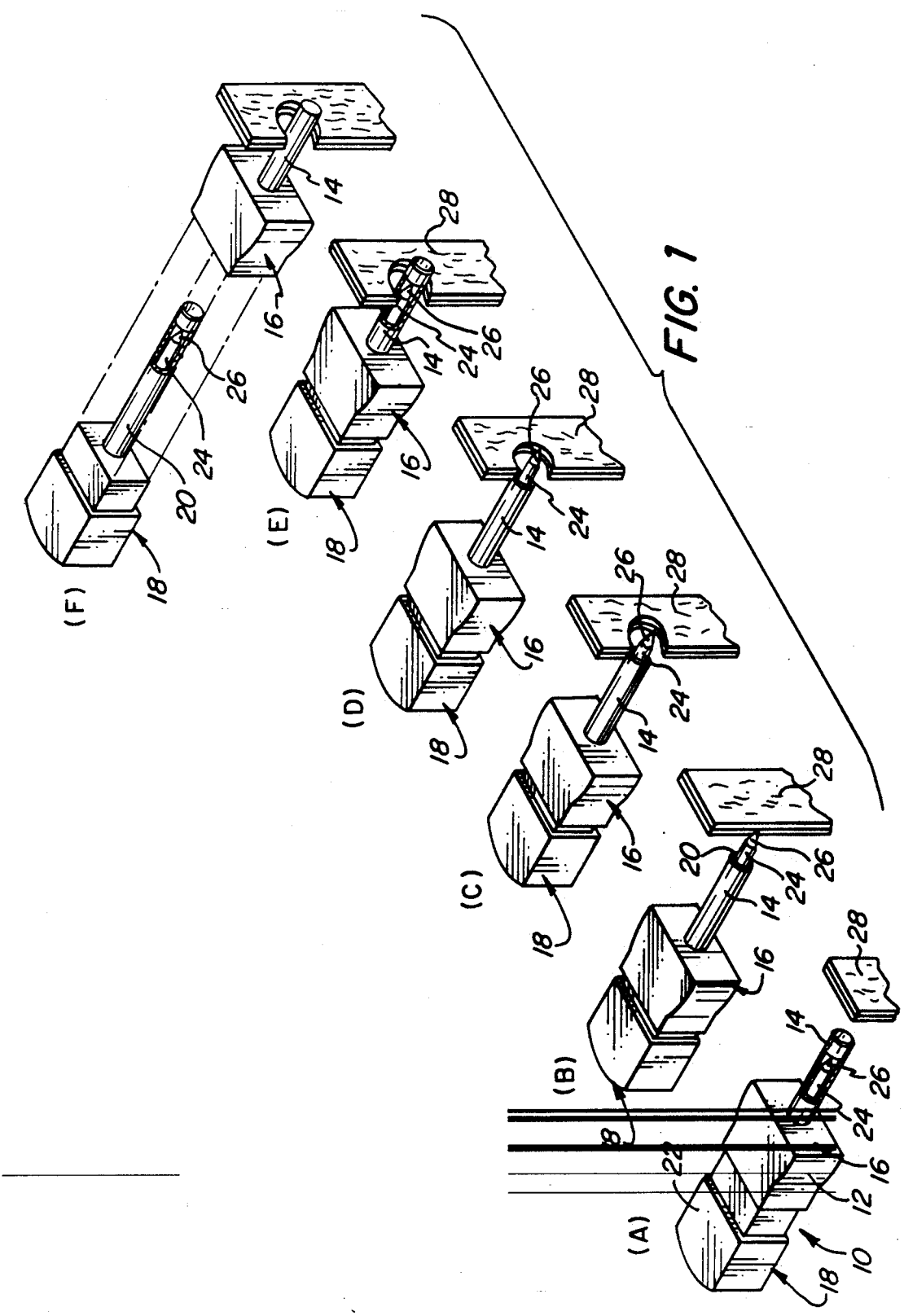
FIG. 1 (A to F) is a sequence of perspective views of the preferred embodiment of the safety trocar instrument of the present invention showing it at various stages during use.

FIGS. 1A though 1F diagrammatically show the safety trocar instrument in accordance with the preferred embodiment of the present invention as it appears in various stages of use. More particularly, this safety trocar instrument, generally indicated at 10, includes a main body 12 having an outer tubular sleeve or cannula 14 projecting from it. The main body-cannula subassembly, generally indicated at 16, is configured to mate with a trocar subassembly generally indicated at 18, that includes a sleeve 20, mounted in a housing 22, and an elongate trocar 24, having a sharp point 26 and being mounted for axial reciprocal movement in the sleeve 20 but being urged to a retracted position therein.

In the assembled rest position of the instrument 10 shown in FIG. 1A, in which the sleeve 20 and cannula 14 are partly broken away to show the location of the trocar point 26, the trocar subassembly 18 is mated with the main body-cannula subassembly 16 such that the coaxially arranged trocar 22 and sleeve 20 are in turn received coaxially within the cannula 14. As can be seen, in this rest position the distal end of the sleeve resides entirely within the distal end of the cannula and the sharp point 26 of the trocar resides within the distal end of the sleeve 20. Thus, in the rest position the sleeve and cannula 14 shield the trocar point 26.

The assembled instrument is armed, as shown in FIG. 1B, to pierce an anatomical wall diagrammatically illustrated at 28, by manually squeezing the trocar subassembly 18 into the main body-cannula subassembly 16. This operation causes the sharp trocar point 26 to project beyond the distal ends of both the sleeve 20 and cannula 14. The trocar is latched in this fully extended position by an internal latching mechanism but is permitted partially to retract from the fully extended position by a lost-motion coupling. Both the latching mechanism and lost-motion coupling will be described in detail below. Thus the trocar point is exposed in preparation for puncturing the cavity wall 28.

As shown in FIGS. 1B and 1C, the trocar point 26 is visible to a surgeon so that it can be precisely positioned at the desired location on an anatomical cavity wall 28 for the intended puncture wound. As the point begins penetration, counterforce exerted by the wall 28 urges the trocar 24 back toward, but not withdrawn into, the distal end of the cannula to an intermediate retracted position as permitted by the lost-motion coupling. In this intermediate position, a trip mechanism is prepared to disarm the internal latching mechanism.

FIG. 1D shows the state of the trocar instrument 10 in which both the trocar point 26 and the distal ends of the sleeve 20 and cannula 14 have cleared the inside surface of the wall 28. Accordingly, the counterforce exerted by the wall on the trocar is relieved permitting it again to be projected to its fully extending position. This action causes the trip mechanism to disarm the internal latch mechanism permitting the trocar to be retracted to its rest position with the trocar point 26 shielded within the sleeve 20 and cannula 14 distal ends, as shown in FIG. 1E. In FIG. 1E the sleeve 20 and cannula 14 are shown partly broken away for clarity as in FIG. 1A.

Finally, as shown in FIG. 1F, the trocar subassembly 18 can be withdrawn from the main body-cannula subassembly 16 with the cannula 14 remaining in the puncture wound in the wall 28. The cannula thus provides a passage through the cavity wall into the cavity interior.

The specific structure of the safety trocar instrument 10 in accordance with a preferred embodiment of the present invention will now be described with reference to FIG. 2, which is a vertical cross-sectional view thereof. The trocar device includes the main body 12 having the cannula 14 extending therefrom. The main body 12 is formed with an intermediate partition 30, an upwardly projecting stop 32 on the partition 30, and a captured compression spring 34. The main body 12 is also formed with a generally rectangularly shaped socket 36 projecting upwardly from the partition 30.

The trocar subassembly 18 is configured to mate with main body-cannula subassembly 16 and includes a main housing 38 having an integrally formed plunger head 40, and the sleeve 20, which has a radial flange 42 at its proximal end and is mounted for reciprocal movement within the housing 38. The bottom of the main housing 38 is rectangularly shaped to be telescopically received in the socket 36.

The trocar 24 is mounted for axial reciprocal movement within the trocar subassembly and includes a shaft 52 having radially projecting upper and lower flanges 54 and 55 near its proximal end and the sharp point 26 at its distal end. The trocar shaft 52 is coaxially received within the sleeve 20. A stop plate 50 is received about the trocar shaft 52 between the upper and lower flanges 54 and 55 and is urged upwardly into contact with the upper radial flange 54 by a pressure spring 57. The stop plate 50, pressure spring 57, and flanges 54 and 55 constitute a lost-motion coupling, the function of which will be described in further detail below.

The trocar 24 is urged to a retracted rest position by a retractor spring 56 compressed between the lower side of the stop plate 50, which engages the upper flange 54, and the sleeve flange 42. The trocar 24 is also stopped in this retracted rest position by a pair of pivotable pushers 58 mounted in the plunger head 40 that, when closed in the radial direction, engage the proximal end 59 of the trocar shaft 52, which has a reduced diameter. The pivotable pushers 58 each have a downwardly, radially outwardly tapered outer cam surface 60 that is engaged by an inner aperture in an embracing ring 62 mounted in the plunger head 40. The ring 62 is urged downwardly by a plunger spring 64 that is compressed between it and the inner surface of the top 65 of the plunger head 40. The embracing ring 62, which thus constitutes a cam driver, urges the pivotable pushers 58 radially together by engaging the tapered outer pusher surfaces 60.

In addition, the trocar subassembly incorporates a latch mechanism the function of which was generally described above. Now, in detail, this latch mechanism includes latch means in the form of a pawl 68 mounted for pivoted movement on the sleeve flange 42, and an upstanding tab 76 projecting upwardly from the intermediate partition 30 in the main body through a hole in the bottom of the main housing. The pawl 68 is formed with a hook 72 at its upper end, which can override and engage an upper edge of the stop plate 50, and a foot 78 at its lower end that can engage a catch 79 at the upper end of the tab 76.

A trip mechanism for the latch mechanism, comprising the tab 76 and pawl 68, includes an arm 74 pivotably mounted in the plunger head. The arm 74 has a tab 71, which can be engaged by the lower edge of the lower flange 55 to cause the arm 74 to pivot in the counterclockwise direction, and a finger 73, which can engage the foot 78 of pawl 68. It is these latch and trip mechanisms, in cooperation with the trocar flanges 54 and 55 and the stop plate 50, that determine the sequence of operations of the trocar instrument described above with reference to FIGS. 1A to 1F.

More particularly, FIGS. 3A through 3D show the sequence of movements of the various elements of the safety trocar instrument described above from the rest position to arming of the instrument, and, in turn, to initial penetration of the anatomical cavity wall.

Figure 2:
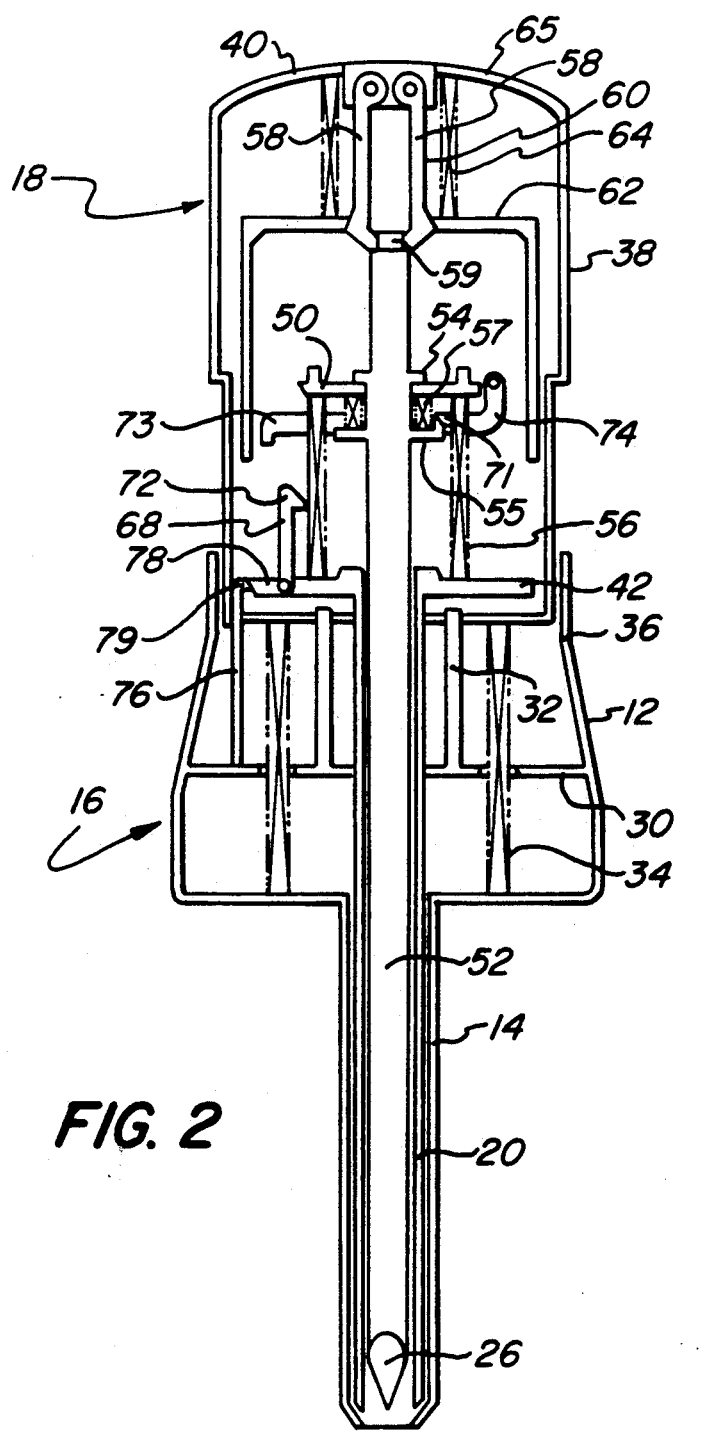
FIG. 2 is a vertical cross-sectional view of the safety trocar instrument of the present invention shown in its assembled rest condition.

In the initial rest position shown in FIG. 3A, which is substantially the same as FIG. 2, the trocar subassembly 18 is inserted into the main body-cannula subassembly 16 with the sleeve 20 and trocar shaft 52 coaxially received within the cannula 14. The distal ends of the sleeve 20 and cannula 14 terminate at nearly the same axial location, with the main housing 38 being urged outwardly from the main body 12 to its rest position by the relaxed compression spring 34.

When the device is to be used, the trocar subassembly 18 is manually squeezed into main body-cannula subassembly 16 thereby compressing the captured spring 34, until the catch 79 of the tab 76 catches the foot 78 of the pawl 68 with the sleeve flange 42 abutting the stop 32, which projects through holes in the bottom of the main housing 38. At this stage, the trocar shaft is moved downwardly a small distance by the pushers 58, but the trocar point 26 remains within both the sleeve 20 and cannula 14, as shown in FIG. 3B.

Further depression of plunger head 40 relative to the main housing 38 causes the pivotable pushers 58 to push the trocar shaft 54 axially downwardly further until the hook 72 of the pawl 68 overrides and catches the edge of the stop plate 50 thereby compressing the retractor spring 56. At this stage the trocar point 26 projects to a fully extended position beyond the distal ends of both the sleeve 20 and cannula 14, as shown in FIG. 3C. Those distal ends also become substantially coextensive.

Ultimately, complete depression of plunger head 40 causes the sidewall of the embracing ring 62 to engage the periphery of the sleeve flange 42, which as noted has come to rest on the top of a stop 32 projecting upwardly from the intermediate partition 30. Therefore, further downward movement of the plunger head 40 causes the embracing ring 62 to move upwardly relative to the pushers 58, which are then permitted to spread radially outwardly and release the proximal end 59 of the trocar shaft 52. In this configuration, shown in FIG. 3C, the trocar instrument is armed and ready to pierce an anatomical cavity wall.

The instrument can then create a puncture wound by pressing the point 26 of the trocar 24 against the cavity wall. As the point begins its entry, resistance or counterforce exerted by the wall causes the trocar shaft 52 to be urged inwardly into cannula 14 and sleeve 20, against the force of the pressure spring 57, to an intermediate retracted position until the edge of the lower flange 55 overrides the tab 71 of arm 74, as shown in FIG. 3D. The upper and lower flanges 54 and 55 in cooperation with the pressure spring 57 permit this lost trocar motion relative to the stop plate 50.

FIGS. 4A to 4D show the sequence of movement of the various elements of the safety trocar instrument as the cavity wall is penetrated and retraction of the trocar point 26 is subsequently triggered. As depicted in FIG. 4A, counterforce against the point 26 of the trocar shaft 52 is relieved when the trocar and cannula 14 clear the inner surface of the cavity wall. Therefore, the pressure spring 57 may urge the trocar shaft 52 downwardly again from the intermediate position toward the fully extended position. This motion of the trocar causes the arm 74 to be pivoted in the counterclockwise direction by engagement of the edge of the lower flange 55 with the tab 71. The extreme end of the arm 74 then depresses the foot 78 of pawl 68 causing it also to pivot in the counterclockwise direction to disengage its hook 72 from the edge of the stop plate 50, thereby releasing the stop plate 50. The retractor spring 56 compressed between the flange 42 and the stop plate 50 then urges the trocar shaft 52 upwardly into the sleeve 20 and cannula 14 to its withdrawn rest position with the point shielded within the distal ends of both, as depicted in FIG. 4B.

When the plunger head 40 is thereafter manually released, it may move upwardly within the main housing 38 under the influence of compressed spring 34, disengaging the sidewall of the embracing ring 62 from the periphery of the sleeve flange 42. The ring 62 may then be urged downwardly to embrace the pushers 58 and urge them together. The pushers may then again grip the proximal end 59 of the trocar shaft 52, as shown in FIG. 4C. As can also be seen there, the pawl 68 can swing about its pivot so that the foot 78 can be disengaged from the catch 79 of the leg 76.

Thereafter the trocar subassembly may be removed from the main body-cannula subassembly such that the cannula remains in the anatomical cavity wall to provide communication with the cavity interior.

It should be noted that the sleeve 20 in the trocar subassembly is long enough in the preferred embodiment to shield the trocar point, particularly when the trocar subassembly is in its rest condition and removed from the main body-cannula subassembly. However, the sleeve 20 may be eliminated if desired since it, by itself, is not necessary to retraction of the trocar point into the distal end of the cannula. If the sleeve is eliminated, the cannula will shield the trocar point after it is retracted following cavity penetration.

Accordingly, it will be appreciated that the present invention provides an improved safety trocar instrument that retracts a sharpened trocar point into a shielding sleeve as soon as the point of the trocar penetrates an anatomical cavity wall. The instrument may be self-contained and is mechanically actuated. Therefore, reliable operation does not depend on external power supplies or electrical triggering mechanisms.

Although a specific embodiment of the present invention has been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A safety trocar instrument for piercing the wall of an anatomical cavity to provide communication with the inside of the cavity, said trocar instrument comprising:
   (a) a tubular cannula;
   (b) an elongate trocar, having a sharp piercing point, mounted for axial reciprocal movement within said cannula between a withdrawn rest position in which said point is received within and shielded by the distal end of said cannula, a fully extended position in which said point is exposed beyond the distal end of said cannula, and an intermediate position retracted toward the rest position from the fully extended position in which said point is also exposed beyond the distal end of said cannula;
   (c) means for biasing said trocar to its withdrawn position;
   (d) latch means for latching said trocar, in opposition to said biasing means, for reciprocal movement between the fully extended position and the intermediate position; and
   (e) trip means coupling said trocar to said latch means when said trocar moves from the fully extended position to the intermediate position, and tripping said latch means when said trocar returns toward said fully extended position to unlatch said trocar and thereby permit said trocar to be moved to the withdrawn rest position by said biasing means.

2. The safety trocar instrument according to claim 1, further comprising means for urging said trocar from the intermediate position toward the fully extended position when said trocar is latched by said latch means.

3. The safety trocar instrument according to claim 1, wherein said trocar further comprises lost-motion coupling means for coupling said trocar to said latch means and including upper and lower flanges mounted in the region of the proximal end of said trocar and a stop plate mounted on said trocar for reciprocal movement between said upper and lower flanges.

4. The safety trocar instrument according to claim 3, further comprising a catch mounted in fixed position relative to said cannula, and wherein said latch means comprises a pawl for linking said catch and said stop plate when said trocar is moved to the fully extended position.

5. The safety trocar instrument according to claim 4, wherein said trip means comprises a trip arm mounted to engage said trocar when said trocar is moved from the fully extended position to the intermediate position and to unlink said pawl from said stop plate when said trocar is returned toward the fully extended position from the intermediate position.

6. The safety trocar instrument according to claim 1, further comprising plunger means for manually moving said trocar from the withdrawn rest position to the fully extended position.

7. The safety trocar instrument according to claim 6, wherein said plunger means comprises means for gripping a portion of said trocar remote from said piercing point when said trocar is in the withdrawn rest position and for releasing said remote portion when said trocar reaches the fully extended position.

8. The safety trocar instrument according to claim 7, wherein said plunger means further comprises a plunger head mounted for reciprocal movement relative to said trocar, and wherein said gripping means comprises at least one pusher element mounted in said plunger head, and means for driving said pusher element to grip said trocar in a radial direction and to release said trocar.

9. The safety trocar instrument according to claim 8, wherein said trocar and said plunger head are mounted for reciprocal movement in the same axial direction;
   wherein said pusher element has an outer cam surface and is mounted within said plunger head for pivoted movement into and out of gripping engagement with said trocar; and wherein said driving means comprises a cam driver mounted in said plunger head cooperating with said cam surface in a first position to hold said pusher element in gripping engagement with said trocar and in a second position to release said pusher element from gripping engagement with said trocar.

10. The safety trocar instrument according to claim 1, wherein said trocar, said biasing means, and said trip means constitute a trocar subassembly that is removable as a unit from said cannula.

11. A safety trocar instrument for piercing the wall of an anatomical cavity to provide communication with the inside of the cavity, said trocar instrument comprising:
   (a) a tubular cannula;
   (b) an elongate trocar, having a sharp piercing point, mounted for axial reciprocal movement within said cannula between a withdrawn rest position in which said point is received within and shielded by the distal end of said cannula and a fully extended position in which said point is exposed beyond the distal end of said cannula;
   (c) means for biasing said trocar to its withdrawn position;
   (d) latch means for latching said trocar in opposition to said biasing means; and
   (e) trip means for tripping said latch means to unlatch said trocar and thereby permit said trocar to be moved to its withdrawn rest position by said biasing means; and
   (f) lost-motion coupling means coupling said trip means to said trocar and permitting said trocar, when latched by said latch means, to reciprocate between the fully extended position and an intermediate retracted position in which said trocar point is also exposed beyond the distal end of said cannula, said trocar arming said trip means when moved to the intermediate retracted position and actuating said trip means to trip said latch means when returned toward the fully extended position.

12. The safety trocar instrument according to claim 11, wherein said trocar arms said trip means when said trocar is moved to the intermediate retracted position by counterforce on said trocar point and thereafter actuates said trip means to trip said latch means when counter force is relieved from said trocar point.

13. The safety trocar instrument according to claim 11, wherein said coupling means comprises means for urging said trocar toward the fully extended position from the intermediate retracted position when said trocar is latched by said latch means.

14. The safety trocar instrument according to claim 11, further comprising a housing in which said trocar is mounted for said reciprocal movement, and a catch mounted in fixed position relative to said cannula, and wherein said latch means comprises a pawl pivot mounted within said housing to link said catch and said trocar together when said trocar is moved to the fully extended position.

15. The safety trocar instrument according to claim 14, wherein said trip means includes an arm pivotably mounted within said housing to be coupled to said trocar when said trocar is moved to the intermediate retracted position as permitted by said lost-motion coupling means, and to disengage said pawl from said catch when said trocar returns toward said fully extended position.

16. The safety trocar instrument according to claim 15, wherein said lost-motion coupling means comprises upper and lower flanges mounted in the region of the proximal end of said trocar and a stop plate mounted on said trocar for reciprocal movement between said upper and lower flanges, wherein said pawl includes a hook engageable with said stop plate when said trocar is moved to its fully extended position.

17. The safety trocar instrument according to claim 11, further comprising a housing, and a catch mounted in fixed position relative to said cannula, and wherein said latch means comprises a pawl pivotably mounted within said housing to link said catch and said trocar together when said trocar is moved to its fully extended position;
   said trip means comprises an arm pivotably mounted within said housing to be coupled to said trocar when said trocar is moved to the intermediate retracted position as permitted by said lost-motion coupling means, and to disengage said pawl from said catch when said trocar is returned toward the fully extended position; and
   said lost-motion coupling means comprises upper and lower flanges mounted in the region of the proximal end of the trocar and a stop plate mounted on said trocar for reciprocal movement between said upper and lower flanges.

18. A safety trocar instrument according to claim 17, further comprising means for urging said trocar toward the fully extended position from the intermediate retracted position when said trocar is latched by said latch means.

19. The safety trocar instrument according to claim 11, further comprising plunger means for manually moving said trocar from the withdrawn rest position to the fully extended position.

20. The safety trocar instrument according to claim 19, wherein said plunger means comprises means for gripping a portion of said trocar remote from said piercing point when said trocar is in the withdrawn rest position and for releasing said remote portion when said trocar reaches the fully extended position.

21. The safety trocar instrument according to claim 20, wherein said plunger means further comprises a plunger head mounted for reciprocal movement relative to said trocar, and wherein said gripping means comprises at least one pusher element mounted in said plunger head, and means for driving said pusher element to grip said trocar in a radial direction and to release said trocar.

22. The safety trocar instrument according to claim 21, wherein said trocar and said plunger head are mounted for reciprocal movement in the same axial direction; wherein said pusher element has an outer cam surface and is mounted within said plunger head for pivoted movement into and out of gripping engagement with said trocar; and wherein said driving means comprises a cam driver mounted in said plunger head cooperating with said cam surface in a first position to hold said pusher element in gripping engagement with said trocar and in a second position to release said pusher element from gripping engagement with said trocar.

23. The safety trocar instrument according to claim 21, wherein said trocar, said biasing means, and said trip means constitute a trocar subassembly that is removable as a unit from said cannula.

24. A safety trocar instrument for piercing the wall of an anatomical cavity to provide communication with the inside of the cavity, said trocar instrument comprising:
  (a) a main body-cannula subassembly including:
    (1) a main body;
    (2) a tubular cannula projecting from the main body; and
  (b) a trocar subassembly formed to mate with said main body-cannula subassembly and including:
    (1) a housing;
    (2) an elongate trocar, having a sharp piercing point, mounted for axial reciprocal movement relative to said housing between a withdrawn rest position, a fully extended position, and an intermediate position retracted from the fully extended position toward the withdrawn position, said trocar being formed to be coaxially received in said cannula with said point exposed beyond the distal end thereof in the fully extended and intermediate positions, and with said point withdrawn into and shielded by the distal end of said cannula in the withdrawn position;
    (3) means for biasing said trocar toward its withdrawn position;
    (4) plunger means with which said trocar subassembly can be manually urged toward said main body-cannula subassembly to an armed stage to move said trocar to its fully extended position;
    (5) latch means for latching said trocar, in opposition to said biasing means, for reciprocal movement between the fully extended position and the intermediate position when the instrument is in the armed stage; and
    (6) trip means coupling said trocar to said latch means when said trocar moves from the fully extended position to the intermediate position in the armed stage, said trip means thereafter tripping said latch means when said trocar returns toward the fully extended position from the intermediate position thereby to permit said trocar to be urged to its withdrawn position by said biasing means.

* * * * *